United States Patent [19]
Chuter

[11] Patent Number: 5,993,482
[45] Date of Patent: Nov. 30, 1999

[54] FLAT WIRE STENT

[75] Inventor: Timothy A. M. Chuter, San Diego, Calif.

[73] Assignee: EndoVascular Technologies, Inc., Menlo Park, Calif.

[21] Appl. No.: 08/885,830

[22] Filed: Jun. 30, 1997

Related U.S. Application Data

[63] Continuation of application No. 08/582,943, Jan. 4, 1996, abandoned.

[51] Int. Cl.$^6$ ................................................. A61F 2/06
[52] U.S. Cl. ................................................................ 623/1
[58] Field of Search .................................. 623/1, 11, 12; 606/192, 194, 195, 198

[56] References Cited

U.S. PATENT DOCUMENTS

| | | | |
|---|---|---|---|
| 4,214,587 | 7/1980 | Sakura, Jr. ........................... | 128/334 R |
| 4,503,569 | 3/1985 | Dotter . | |
| 4,553,545 | 11/1985 | Maass . | |
| 4,580,568 | 4/1986 | Gianturco . | |
| 4,655,771 | 4/1987 | Wallsten . | |
| 4,733,665 | 3/1988 | Palmez . | |
| 4,739,762 | 4/1988 | Palmez . | |
| 4,787,899 | 11/1988 | Lazarus ......................................... | 623/1 |
| 4,820,298 | 4/1989 | Leveen et al. ............................... | 623/1 |
| 4,830,003 | 5/1989 | Wolff et al. . | |
| 4,886,062 | 12/1989 | Wiktor . | |
| 4,913,141 | 4/1990 | Hillstead . | |
| 4,990,155 | 2/1991 | Wilkoff . | |
| 5,015,253 | 5/1991 | MacGregor . | |
| 5,019,085 | 5/1991 | Hillstead . | |
| 5,019,090 | 5/1991 | Pinchuk . | |
| 5,037,427 | 8/1991 | Harada et al. . | |
| 5,104,404 | 4/1992 | Wolff . | |
| 5,133,732 | 7/1992 | Wiktor . | |
| 5,135,536 | 8/1992 | Hillstead . | |
| 5,192,307 | 3/1993 | Wall ........................................... | 623/1 |
| 5,222,971 | 6/1993 | Willard et al. . | |
| 5,226,913 | 7/1993 | Pinchuk . | |
| 5,316,023 | 5/1994 | Palmez et al. ........................... | 128/898 |
| 5,331,027 | 7/1994 | Whitbourne ............................... | 524/37 |
| 5,342,348 | 8/1994 | Kaplan .................................. | 604/891.1 |
| 5,342,387 | 8/1994 | Summers ................................. | 606/198 |
| 5,366,504 | 11/1994 | Andersen et al. ........................ | 623/11 |
| 5,370,683 | 12/1994 | Fontaine . | |
| 5,383,892 | 1/1995 | Cardon et al. ........................... | 606/198 |
| 5,383,925 | 1/1995 | Schmitt ...................................... | 623/1 |
| 5,415,664 | 5/1995 | Pinchuk ................................... | 606/108 |
| 5,423,885 | 6/1995 | Williams ..................................... | 623/1 |
| 5,441,515 | 8/1995 | Khosravi et al. ....................... | 606/194 |
| 5,443,907 | 8/1995 | Slaiken et al. ............................ | 428/375 |
| 5,474,563 | 12/1995 | Myler et al. .............................. | 606/108 |
| 5,476,508 | 12/1995 | Amstrup ...................................... | 623/1 |
| 5,490,839 | 2/1996 | Wang et al. ............................... | 604/96 |
| 5,507,767 | 4/1996 | Maeda et al. ........................... | 606/198 |
| 5,514,154 | 5/1996 | Lau et al. ................................ | 606/195 |
| 5,527,354 | 6/1996 | Fontaine et al. ........................ | 606/154 |
| 5,527,355 | 6/1996 | Ahn ............................................ | 623/1 |
| 5,540,712 | 7/1996 | Kleshinski et al. ..................... | 606/198 |
| 5,549,663 | 8/1996 | Cottone, Jr. ................................ | 623/1 |
| 5,562,726 | 10/1996 | Chuter ........................................ | 623/1 |
| 5,571,170 | 11/1996 | Palmaz et al. ............................. | 623/1 |
| 5,591,197 | 1/1997 | Orth et al. ................................ | 606/198 |
| 5,591,228 | 1/1997 | Edoga ......................................... | 623/1 |
| 5,603,721 | 2/1997 | Lau et al. ................................. | 606/195 |
| 5,609,627 | 3/1997 | Goicoechea et al. ...................... | 623/1 |
| 5,613,979 | 3/1997 | Trotta et al. ........................... | 606/194 |
| 5,617,878 | 4/1997 | Taheri ..................................... | 128/898 |

(List continued on next page.)

OTHER PUBLICATIONS

Description of Hexstent by Applicant, T.A.M. Chuter.

*Primary Examiner*—Michael J. Milano
*Attorney, Agent, or Firm*—Fulwider, Patton, Lee & Utecht, LLP

[57] ABSTRACT

The present invention concerns an improved stent in which the limbs have been fabricated from a medium having a cross sectional profile in which at least one segment is flat and straight, whereby the stent is provided with improved expansion characteristics.

13 Claims, 4 Drawing Sheets

U.S. PATENT DOCUMENTS

| | | | |
|---|---|---|---|
| 5,628,782 | 5/1997 | Myers et al. | 623/1 |
| 5,628,788 | 5/1997 | Pinchuk | 623/1 |
| 5,630,829 | 5/1997 | Lauterjung . | |
| 5,632,763 | 5/1997 | Glastra | 606/194 |
| 5,645,532 | 7/1997 | Horgan | 604/117 |
| 5,649,949 | 7/1997 | Wallace et al. | 606/191 |
| 5,649,951 | 7/1997 | Davidson | 606/198 |
| 5,667,523 | 9/1997 | Bynon et al. | 606/198 |
| 5,741,327 | 4/1998 | Frantzen | 623/12 |
| 5,746,691 | 5/1998 | Frantzen | 623/901 |

FLAT WIRE STENT

This application is a continuation-in-part of application Ser. No. 08/582,943, filed Jan. 4, 1996, now abandoned.

FIELD OF THE INVENTION

The present invention relates to an improved "stent" for placement in corporeal lumens. More particularly, this invention relates to an improved stent in which the limbs have been fabricated from a medium having a cross sectional profile in which at least one segment is straight, whereby the stent is provided with improved expansion characteristics.

BACKGROUND OF THE INVENTION

The term stent generally refers to a prosthesis, which can be introduced into a corporeal lumen and expanded to support that lumen or attach a conduit to the inner surface of that lumen.

A number of prior art references are available in the art, each of which references is directed to some specific discrete elements of the system which are described and claimed in the present invention, however, none of which is directed to the totality of the combination, or its use and function in the manner described and claimed herein.

The following prior art references are known to the inventor:

U.S. Pat. No. 4,580,568, which issued to Gianturco on Apr. 8, 1986, discloses an endovascular stent formed of stainless steel wire which is arranged in a closed zig-zag pattern;

U.S. Pat. No. 4,733,665, which issued to Palmaz on Mar. 29, 1988, relates to an expandable intraluminal vascular graft which is expanded within a blood vessel using an angioplasty balloon associated with a catheter;

U.S. Pat. No. 4,739,762, which issued to Palmaz on Apr. 26, 1988, teaches an expandable intraluminal graft for use within a body passageway or duct which is particularly useful for repairing blood vessels which have been narrowed or occluded by disease;

U.S. Pat. No. 4,830,003, which issued to Wolff et al on May 16, 1989, discloses a cylindrical shaped stent useful to prevent arterial acute closure which is formed of longitudinal wires of biocompatible material, which wires have been welded together in pairs at alternate ends with each pair or wires bent into a V-section. The wires are formed into a cylinder which is welded closed in order to form the stent;

U.S. Pat. No. 5,104,404, which issued to Wolff on Apr. 14, 1992, teaches an intravascular stent which is applied within the peripheral or coronary arteries of a living animal or a human being in order to return patency after a balloon angioplasty. The stent taught in this reference is an articulated separate stent comprising at least two segments, each of which segments has a generally tubular shape and a hinge means extending between and connecting adjoining stent segments;

U.S. Pat. No. 5,019,090, which issued to Pinchuk on May 28, 1991, relates to radially expandable stents which include a plurality of adjacent generally circumferential sections which are substantially axially positioned with respect to each other;

U.S. Pat. No. 4,886,062, which issued to Wiktor on Dec. 12, 1989, discloses a device which is to be used as a vascular stent comprising a cylindrical open-ended wire made of a low memory metal, which is characterized by its ability to be expanded radially to a larger diameter after initial implantation, along with a means for causing said stent to expand to a larger diameter and a method for transporting, positioning and implantation of such stent;

U.S. Pat. No. 5,370,683, which issued to Fontaine on Dec. 6, 1994, is directed to a vascular stent for reducing hemodynamic disturbances caused by angioplasty, said stent being formed from a single filament of low memory biocompatible material having a series of U-shaped bends. The filament is wrapped about a mandril in a circular fashion in order to align the curved portions of each bend which may then be connected;

U.S. Pat. No. 5,226,913, which issued to Pinchuk on Jul. 13, 1993, teaches a radially expandable stent which includes a plurality of adjacent generally circumferential sections that are substantially axially positioned with respect to each other, wherein at least one of the generally circumferential sections has an expandable segment which imparts a circumferential and radial expandability to the stent;

U.S. Pat. No. 4,913,141, which issued to Hillstead on Apr. 3, 1990, relates to a stent delivery system for routing the stent to a defined position within a subject's blood vessel;

U.S. Pat. No. 5,133,732, which issued to Wiktor on Jul. 28, 1992, discloses a stent for implantation into a body vessel comprising a cylindrical stent body which has been coiled from a generally continuous wire which has been imparted with a deformable zig-zag structure;

U.S. Pat. No. 5,135,536, which issued to Hillstead on Aug. 4, 1994, is directed to a stent for reinforcing a vessel wall which is constructed from a single elongated wire. The wire has been first bent into a series of tight bends and then rolled around a mandril in order to create junctions of wire which are permanently adhered. The completed stent forms a cylindrical shape which can be expanded from its initial diameter to a larger implanted diameter by the application of radial outward force from a balloon catheter;

U.S. Pat. No. 4,655,771, which issued to Wallsten on Apr. 7, 1987, teaches a prosthesis for transluminal implantation comprising a flexible tubular body which has a diameter that is variable by axial movement of the ends of the body relative to each other and which is composed of several individual rigid but flexible thread elements each of which extends in helix configuration with the centerline of the body as a common axis;

U.S. Pat. No. 5,015,253, which issued to MacGregor on May 14, 1991, discloses a generally tubular stent that includes a non-woven structure formed by two or more generally helically shaped cylinders of stiff strand material where the strand material forming the non-woven structure is preferably secured together at attachment sites which allow the stent to be flexible and adjustable to meet various needs.

Most manifestations of the available prior art expand by the rotation of a structural element (limb) from a longitudinal orientation (parallel to the long axis of the stent) to a more transverse orientation. The limbs themselves change very little in shape. Stents, in which adjacent limbs are linked to form rings, spirals, or a series of linked rings, expand and contract by deformation of the structural elements in the immediate vicinity of the junction between limbs. In the case of self-expanding stents, the junctions serve as reservoirs of energy, which produce stent expansion. However, the isolation of mechanical stress to such small portions of the stent limits the expansion ratio and renders the stent less durable.

An example of this effect is the Gianturco Z-stent ('568). This stent is comprised of a single loop of wire, in which alternating straight segments wind back and forth between bends to form a crown. In the Ginaturco Z-stent the junctional stresses can be diffused by increasing the radius of curvature at the bends; the larger the bend the more diffuse the stress. However, large radius bends limit the expansion ratio, because the bends take up more space than straight segments. Bending the limbs themselves does little to reduce the stress, because these bends are much less amenable to deformation than the bends between adjacent limbs. When the stent is compressed, the limbs soon meet along the outer curvatures of any bends. Any attempt to further collapse the stent by straightening the limbs is thwarted by the overlapping.

Other stents, which have no rings or spirals of alternating limbs and no fixed junctions between limbs, are free of these problems; however, they also lack the expansile energy provided by junctional deformation, and therefore tend to expand rather weakly. There are currently no self-expanding stents available in the prior art in which the relative positions of the joined limbs change as a result of deformation that is distributed over large segments of the limbs.

It is, therefore, an object of the present invention to provide for an improved stent which exhibits superior expansion characteristics over available prior art stents.

It is a further object of the present invention to provide for an improved stent in which the limb elements have been fabricated from a medium having a cross sectional profile in which at least one segment is flat and straight, which exhibits superior expansion characteristics over available prior art stents.

Lastly, it is an object of the present invention to provide for an improved stent which exhibits superior expansion characteristics over available prior art stents while at the same time avoiding the compression and deformation problems associated with other prior art stents.

These and other objects of the invention will become apparent from the following discussion of the invention.

SUMMARY OF THE INVENTION

The present invention provides for an improved stent in which the limbs have been fabricated from a medium having a cross sectional profile in which at least one segment is straight, whereby the stent is provided with improved expansion characteristics.

The construction and obvious advantages of the system provided for by the present invention will be more clearly understood from the following description of the various specific embodiments when read in conjunction with the accompanying drawings.

BRIEF DESCRIPTION OF THE DRAWINGS

FIG. 7 is a schematic representation of the end of a limb according to the present invention depicting a hole for attachment of a delivery system release mechanism, or the like.

DETAILED DESCRIPTION OF THE INVENTION

The present invention is directed to an improved stent in which the limbs have been fabricated from a material having a cross sectional profile in which at least one segment is straight, whereby the stent is provided with improved expansion characteristics as compared with available prior art stents.

The problems which have been experienced using prior art stents are solved in the present invention by creating the stent limbs from a material, generally a springy wire material, which has a cross-sectional profile in which at least one segment is flat and straight.

Two properties of flat wire are responsible for the principal advantages of this invention:

1. The flat surfaces of adjacent limb segments of the stent can be pressed together without generating the lateral forces that would otherwise cause them to overlap.

2. The mechanical stent limbs can be wide without taking up a large volume. The width of the limb makes it relatively rigid in the plane of its largest diameter, which also helps to prevent overlapping.

Figure 1:
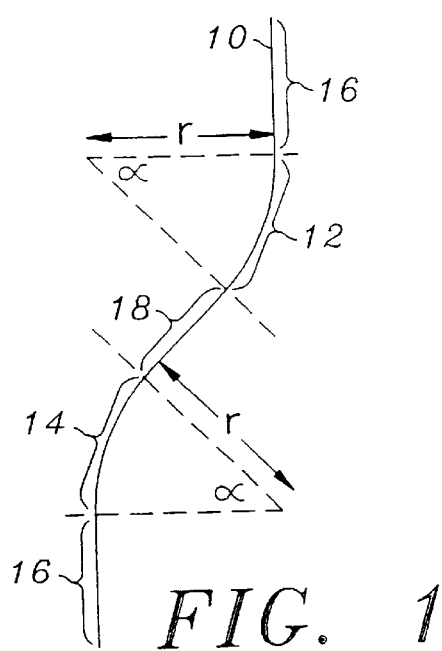
FIG. 1 is a schematic representation depicting a single limb element according to the present invention.
Figure 2:
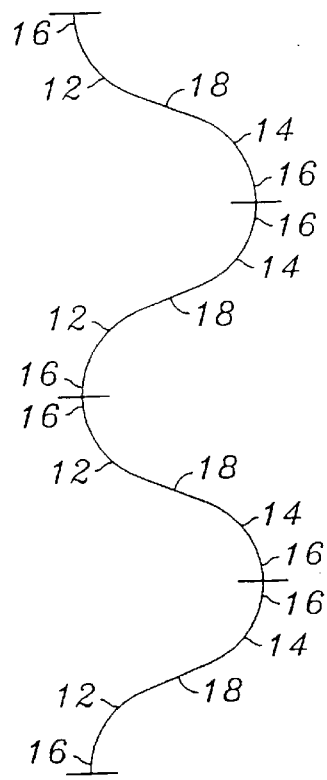
FIG. 2 is a schematic representation depicting a single wire comprising four limb elements according to the present invention.
Figure 3:
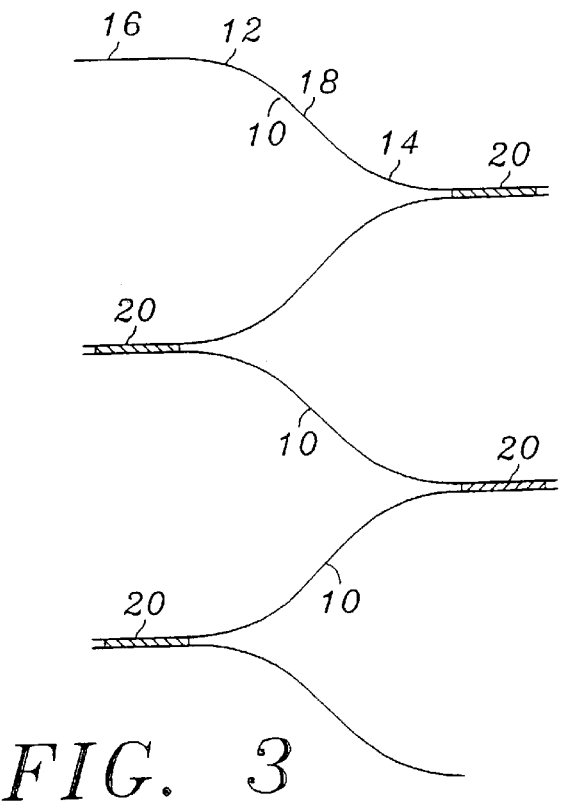
FIG. 3 is a schematic representation depicting typical joints between adjacent limb elements in a stent which is comprised of a multiplicity of such limb elements.
Figure 4A:
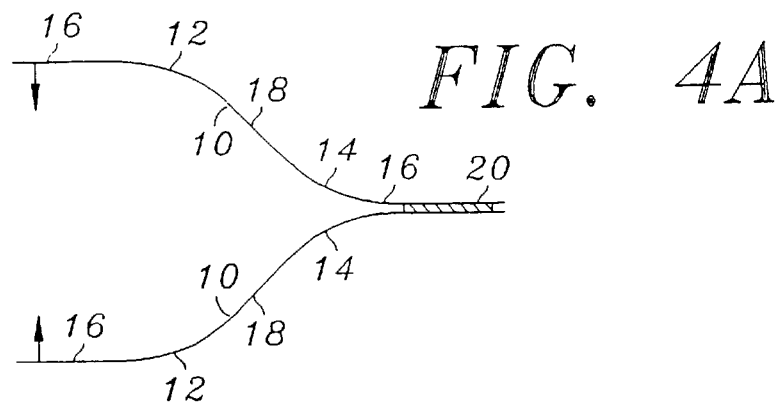
FIGS. 4A–4D is a schematic representation depicting the progressive compression of the joint between adjacent limb elements in a stent.
Figure 4B:
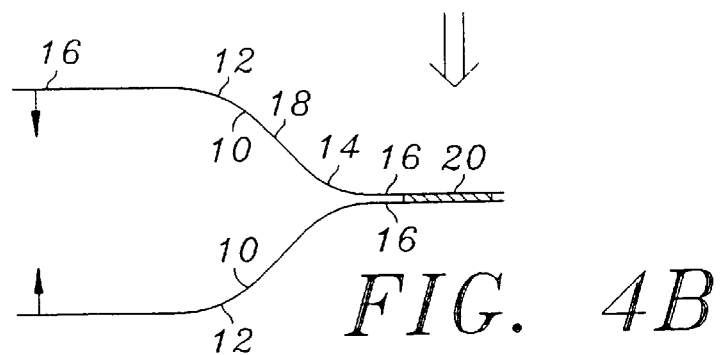
Figure 4C:
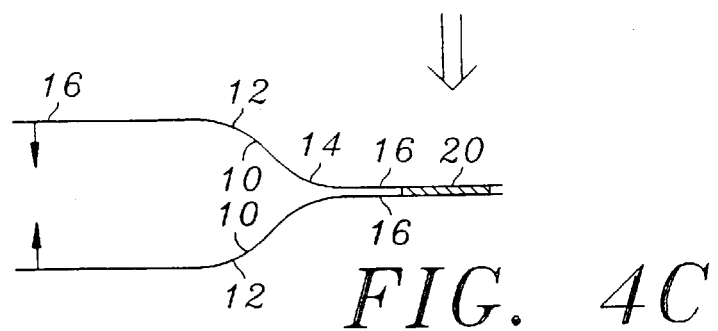
Figure 4D:
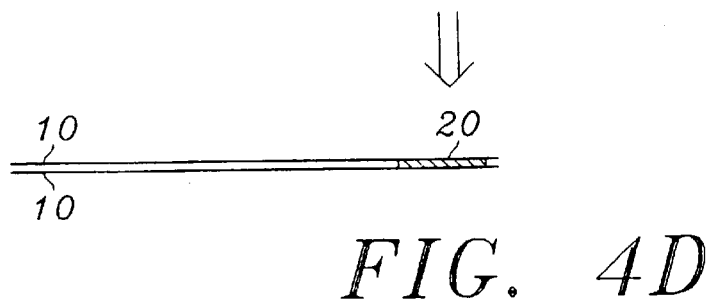
Figure 5:
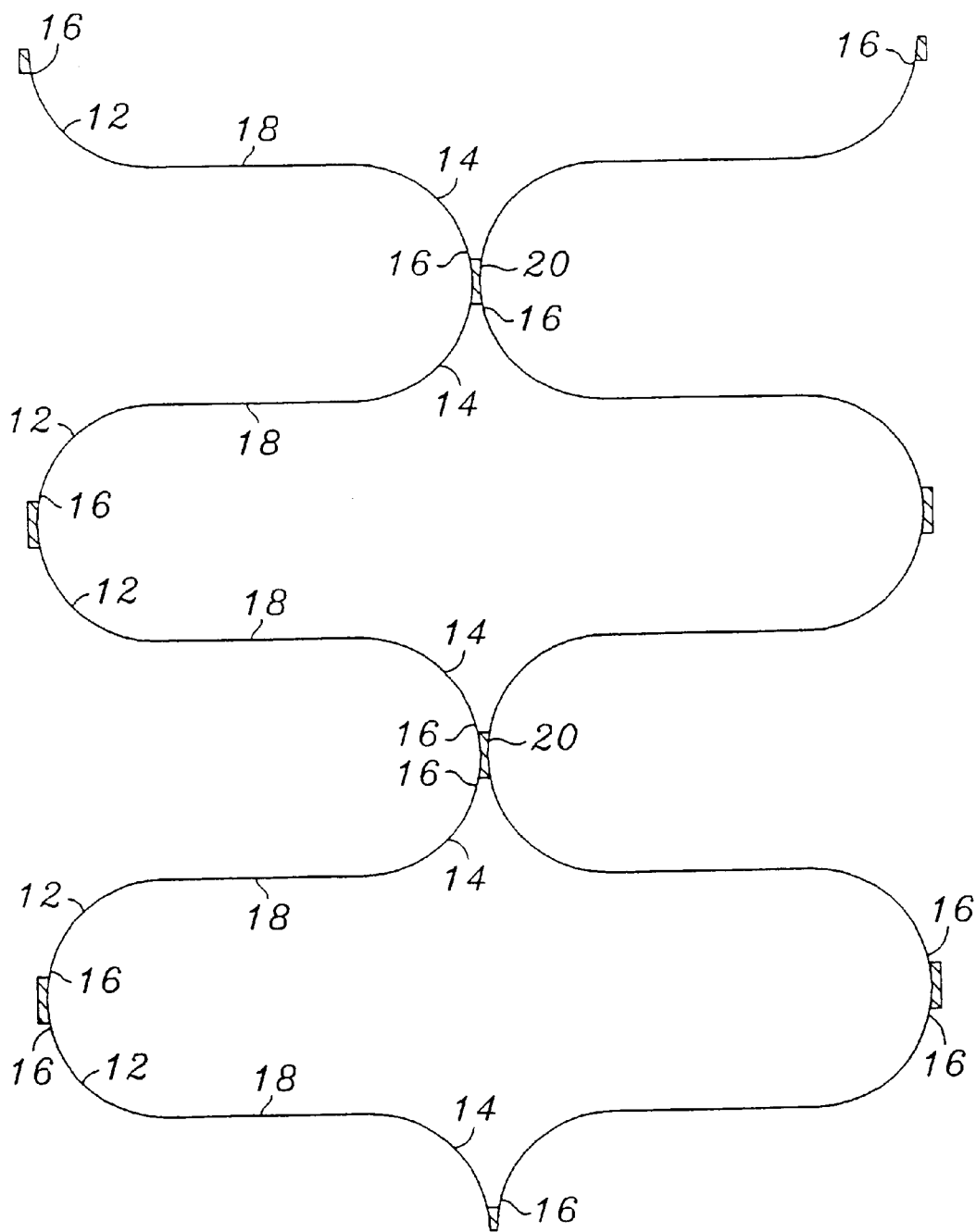
FIG. 5 is a schematic representation of a portion of a stent according to the present invention showing the relative geometry of the curved limb elements and the joints between adjacent limb elements.

With reference to the attached figures, it can be seen from FIGS. 1 and 5 that a repeating element of each limb 10 of the stent has two curves 12 and 14 of equal radius, equal length and opposite direction. The short straight segments 16 at the ends of each limb element are parallel to one another. The mid-portion 18 lies between the two curved segments of each repeating element of the stent limb. Depending on the overall length of the stent, the same piece of wire may bend back and forth in a sinusoid wave, FIG. 2, to form a series of limb elements 10 down the length of the stent.

The short straight segments 16 of adjacent limbs are joined, either by welding, soldering, riveting, or gluing, as depicted in FIGS. 3–9. A multiplicity of identical limb elements are joined in this way to form a cylindrical structure. With reference to FIGS. 3 and 4A–4D, it can be seen that compression of the stent causes adjacent limb elements to be pressed against one another at their junctions 20. Further compression causes the curved portions 12 and 14 of adjacent limb elements to flatten progressively. The curves 12 and 14 thereby straighten and the stent assumes a smaller and smaller radius. When the constraining force is released, the stent expands through re-establishment of the curves 12 and 14.

The flat "wire" which is employed in the present invention can be made of any biocompatible material that is strong, durable and capable of elastic deformation.

The number of limb elements in each length of wire can be varied according to the ratio of length to width required for the specific application in which the stent is to be employed. For example, an extended narrowing, as for example in a corporeal lumen such as an artery, a bile duct or an esophagus would require a stent that is much longer than it is wide. The individual wires in such a stent would therefore have many limb elements 10, many bends 12 and 14, and many joints, since each wire would extend along the entire length of the stent. Alternatively, a stent which is used for anchoring a graft in a short segment of aorta would have very few limb elements 10, perhaps only one, in each length of wire.

The radius and length of the curves 12 and 14 can be altered to effect the orientation of the section of the limb element that lies between the curves, the mid-section 18. In addition the mid-section 18 may vary in length as may be required for the particular application. The greater the angle described by each curve 12 and 14 in the limb element 10, the more transverse the orientation of the mid-section of the limb, the greater the shortening produced by stent expansion, the greater the flexibility of the stent, and the greater the resistance to compression by forces applied in direction of the stent radius. Lengthening the mid-section 18 of the limb element magnifies all of these effects.

Figure 6A:
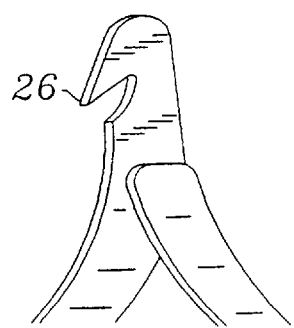
FIG. 6A is a schematic representation of the end of one limb of a stent according to the present invention depicting a barb which has been incorporated therein for anchoring the stent to a lumen wall.

With reference to FIG. 6A, an alternative embodiment of the end of a limb according to the present invention is shown wherein a barb can be added by notching 22 the edge of a limb in order to provide a means for attachment of the limb to the inside of a corporeal lumen.

Figure 6B:
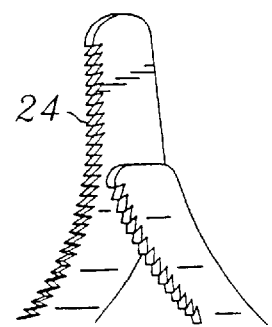
FIG. 6B is a schematic representation of the end of a limb according to the present invention depicting serrations as an alternative for anchoring the stent to a lumen wall.

With reference to FIG. 6B, another alternative embodiment of the end of a limb according to the present invention is depicted, showing serrations 24 as a means for attachment of the limb to the inside of a corporeal lumen.

Figure 7:
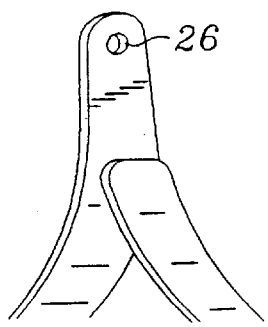
Figure 8:
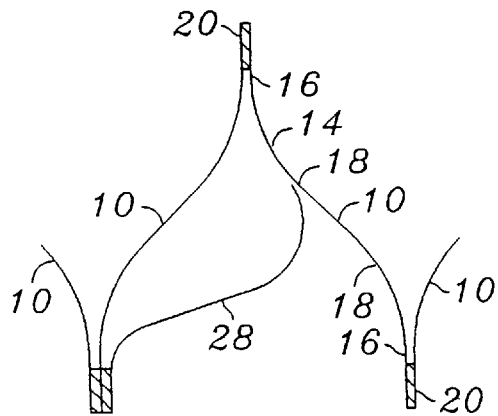
FIG. 8 is a schematic representation of an alternative embodiment of the present invention depicting a simplified series of limb elements which have been attached to adjacent limb elements and the optional addition of a supplemental strut.
Figure 9:
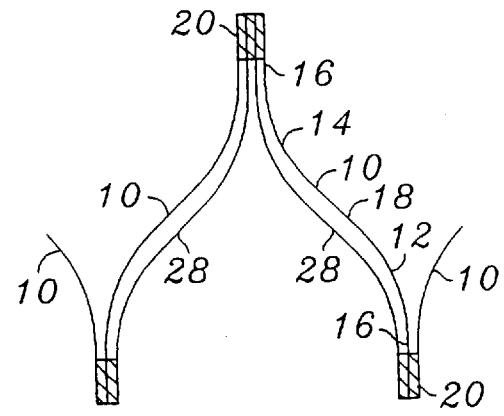
FIG. 9 is a schematic representation of an alternative embodiment of the present invention depicting a simplified series of limb elements which have been attached to adjacent limb elements and the optional addition of two supplemental struts.

With reference to FIG. 7, anchor points for delivery system release mechanisms or for graft attachment are provided for by drilling small holes 26 in the end of the limbs. The optional features weaken the limb but have no effect on the structural integrity of the stent if they are placed in a section of the limb that is not between joints or connections 20.

The centrifugal expansile force generated by large stents can be increased by increasing the thickness of the wire. Alternatively, with reference to FIGS. 8 and 9, optional struts 28 can be added to augment expansion alone, or augment both the expansile force by increasing the rigidity of the composite strut.

It will be further apparent to one skilled in this art that the improvements provided for in the present invention, while described with relation to certain specific physical embodiments, also lend themselves to being applied in other physical arrangements not specifically provided for herein, which are nonetheless within the spirit and scope of the invention taught here.

I claim:

1. A cylindrical stent which is designed to provide superior expansion characteristics within a corporeal lumen comprising a plurality of flat wires extending generally longitudinally along the length of the stent to form a cylindrical stent having an outer surface, each flat wire having a rectangular cross-section with flat wide sides and narrow edge sides, each flat wire comprising at least two limb elements; each limb element comprising two curved portion segments having opposite directions of curvature, an intermediate straight mid-portion segment connecting the two curved portion segments and a short-straight segment connected to each curved portion segment at each end of each limb element; each short-straight segment of each limb element being joined to the adjacent short-straight segment of a limb element of an adjacent flat wire to form the cylindrical stent surface; the flat wide sides of each flat wire being radially perpendicular to the cylindrical stent surface.

2. The improved stent according to claim 1 wherein each wire is equal in length.

3. The improved stent according to claim 1 wherein each limb element is equal in length and configuration.

4. The stent according to claim 1 wherein each wire has a plurality of identical limb elements in series.

5. The stent according to claim 1 wherein each flat wire is bent back and forth in a sinusoidal wave pattern to form a series of limb elements along the length of the wire.

6. The stent according to claim 1 wherein said short-straight segment of said limb element at the end of at least one of said flat wire is elongated and an edge of said elongated short-straight segment is serrated as an anchor point for attachment of the stent to the inside of a corporeal lumen.

7. The stent according to claim 1 wherein said short-straight segment of said limb element at the end of at least one of said flat wire is elongated and barbed as an anchor point for attachment of the stent to the inside of a corporeal lumen.

8. The stent according to claim 1 wherein said short-straight segment of said limb element at the end of at least one of said flat wire is elongated and has a hole as an anchor point for a delivery system release mechanism or a graft attachment.

9. The stent according to claim 1 wherein said short-straight segment of said limb element at the end of at least one of said flat wire is elongated and the edges of said elongated short-straight segment and said adjacent short-straight segment to which it is joined are serrated as an anchor point for attachment of the stent to the inside of a corporeal lumen.

10. The stent according to claim 1 wherein said stent has at least one strut to augment stent expansion and to resist stent compression, said strut having a shorter length than said limb element and having two curved portions having opposite directions of curvature, an intermediate straight, flat mid-portion connecting the two curved portions, and a short-straight segment connected to each curved portion at each end of said strut, one of said short-straight segments of said strut being joined to said short-straight segment of said limb element and lying in said cylindrical stent outer surface, said strut positioned between adjacent limb elements of adjacent wires.

11. A stent according to claim 1 wherein said stent has at least one strut having a length substantially identical to one of said limb elements to augment stent expansion and to resist stent compression, said strut having two curved portions having opposite directions of curvature, an intermediate straight mid-portion connecting said two curved portions, and a short-straight segment connected to said curved portion at each end of said strut, said strut being positioned parallel to said limb element of said short-straight segment the and lying in said cylindrical stent outer surface, said short-straight segment of said strut being attached to said short-straight segment of said limb element.

12. A cylindrical stent which is designed to provide superior expansion characteristics comprising limbs which have been fabricated from a plurality of flat wires having a flat rectangular cross-sectional profile having wide flat sides and narrow edge sides, said limbs being formed out of repeating elements, each limb being comprised of two curved portions having opposite directions of curvature, an intermediate straight mid-portion segment connecting said two curved portions and a short-straight segment at each end of the curved portions, adjacent wires being joined on their wide flat sides by having the short-straight segment of each limb element joined to the short-straight segment of a limb element of an adjacent flat wire to form said cylindrical stent having an outer surface, said stent having been provided with at least one strut in order to augment expansion wherein said strut has been effectively attached at a point of attachment between said adjacent limb elements, each limb element and each strut lying in said cylindrical, stent outer surface said wide, flat sides of each wire being radially perpendicular to said cylindrical stent outer surface.

13. A cylindrical stent which is designed to provide superior expansion characteristics comprising limbs which have been fabricated from a plurality of flat wires having a flat rectangular cross-sectional profile having wide, flat sides and narrow edge sides, said limbs being formed out of repeating elements, each limb being comprised of two curved portions having opposite directions of curvature, an intermediate straight mid-portion segment connecting said two curved portions and a short-straight segment at each end of said curved portions, adjacent wires being joined on their wide flat sides by having the short-straight segment of each limb element joined to the short-straight segment of a limb element of an adjacent flat wire to form said cylindrical stent having an outer surface, said stent having been provided with a multiplicity of struts to supplement each of the limb elements which have been effectively attached at both ends to a point of attachment between adjacent limb elements, each limb element and each strut lying in said cylindrical stent outer surface, said wide, flat sides of each wire being radially perpendicular to said cylindrical stent outer surface.

* * * * *

UNITED STATES PATENT AND TRADEMARK OFFICE
CERTIFICATE OF CORRECTION

PATENT NO. : 5,993,482
DATED : Nov. 30, 1999
INVENTOR(S) : Timothy A. M. Chuter

It is certified that error appears in the above-identified patent and that said Letters Patent is hereby corrected as shown below:

Column 6, line 67, claim 11, after "segment", delete "the".

Signed and Sealed this

Eighteenth Day of July, 2000

Attest:

Q. TODD DICKINSON

Attesting Officer

Director of Patents and Trademarks